United States Patent [19]

Wool

[11] 4,424,033
[45] Jan. 3, 1984

[54] ORTHODONTIC APPLIANCE

[76] Inventor: Arthur L. Wool, 1402 Penn Ave., Wyomissing, Pa. 19610

[21] Appl. No.: 432,777

[22] Filed: Oct. 4, 1982

Related U.S. Application Data

[63] Continuation-in-part of Ser. No. 404,572, Aug. 2, 1982, abandoned, which is a continuation-in-part of Ser. No. 389,017, Jun. 16, 1982, abandoned.

[51] Int. Cl.³ .................................................. A61C 7/00
[52] U.S. Cl. ........................................................ 433/20
[58] Field of Search ...................................... 433/7, 20

[56] References Cited

U.S. PATENT DOCUMENTS

| 678,453 | 7/1901 | Angle | 433/20 |
| 1,773,588 | 8/1930 | Linde | 433/7 |
| 2,318,001 | 5/1943 | Linde | 433/7 |
| 3,916,526 | 11/1975 | Schudy | 433/20 |

*Primary Examiner*—Robert Peshock
*Attorney, Agent, or Firm*—Howson and Howson

[57] ABSTRACT

This orthodontic appliance comprises a novel arch wire having posterior segments of circular cross-section and an anterior segment at least part of which is rectangular or trapezoidal in cross-section. When used in "light wire" treatment, the arch wire is secured to a bracket by a special lock pin having an offset surface on its tail. The offset surface cooperates with the rectangular portion of the anterior segment to prevent relative rotation between the arch wire and the bracket, thereby allowing torqueing. The special lock pin is also used with a uniform rectangular wire to apply torque to posterior teeth having light wire brackets.

14 Claims, 16 Drawing Figures

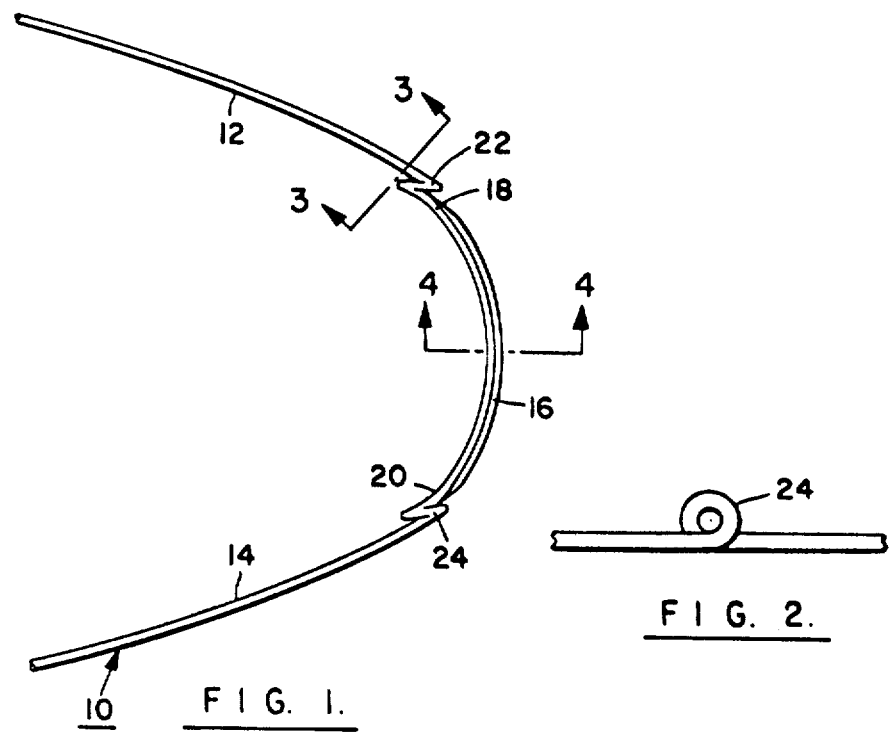
FIG. 1.
FIG. 2.
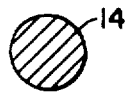
FIG. 3.
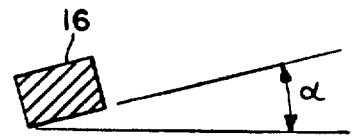
FIG. 4.
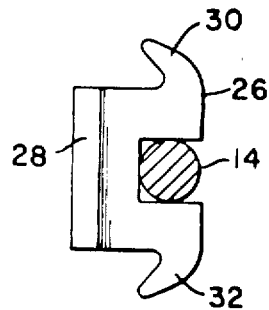
FIG. 5.
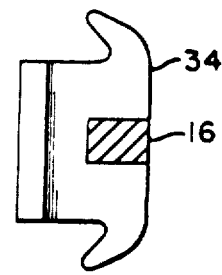
FIG. 6.

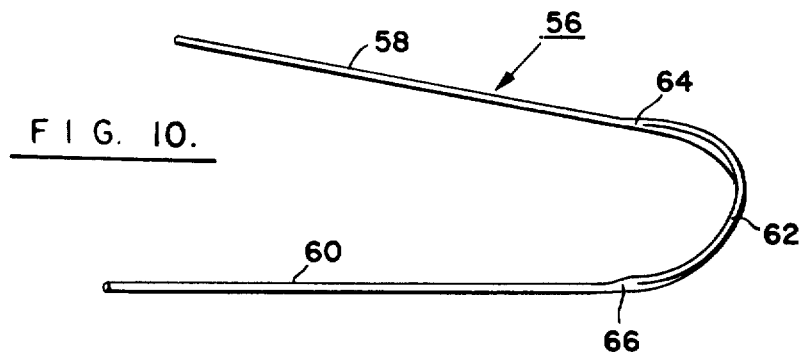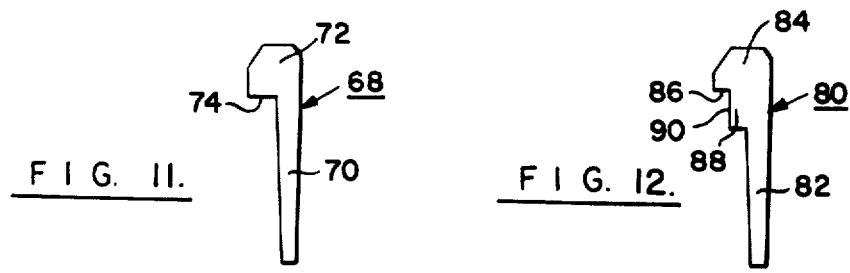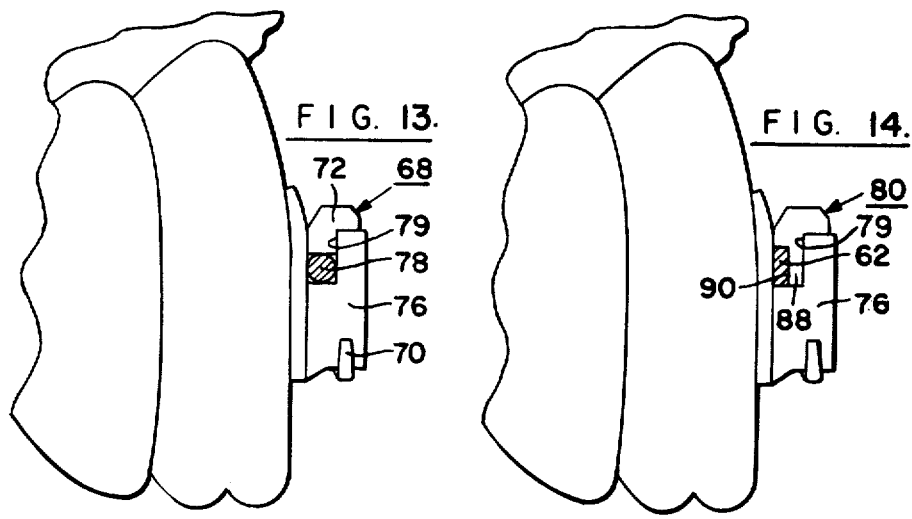

ORTHODONTIC APPLIANCE

CROSS-REFERENCE TO RELATED APPLICATION

This application is a continuation-inpart of my now-abandoned application Ser. No. 404,572, filed on Aug. 2, 1982, which was a continuation-in-part of my abandoned application Ser. No. 389,017, filed on June 16, 1982, both now abandoned.

BRIEF SUMMARY OF THE INVENTION

This invention relates to orthodontic appliances and particularly to improved orthodontic arch wires for more efficient and effective correction of all classes of malocclusions using edgewise or light wire techniques. This invention also relates to improved brackets for use in the light wire technique.

A variety of malocclusions are corrected by the use of orthodontic arch wires. In corrections using arch wires, brackets are secured to the patient's teeth by the use of bands to which the brackets are welded, or by cementing brackets directly to the teeth. Typically, in each of a number of stages during the course of treatment, an arch wire is secured in the brackets. As treatment progresses, the arch wire which is used more closely approaches the ideal arch form. The arch wires progressively correct misalignments of the patient's teeth.

The arch wire not only corrects misalignment of teeth, but also prevents misalignment from occurring as a result of other corrections. An example of another type of correction is the correction of prominent incisors in malocclusions of the second and third classes. These corrections are typically effected by the use of elastic to apply a rearwardly directed force on the entire arch wire. The rearward force on the arch wire has a tendency to cause "tipping", which, if allowed to continue, ultimately causes the incisors to tilt rearwardly toward the back of the mouth, giving the teeth a "dished" appearance. With the edgewise technique, tipping is avoided, and prominent incisors are corrected instead by effecting rearward translation of the teeth. The edgewise technique is characterized by the use of tooth brackets with open rectangular slots together with arch wires having a rectangular cross-section which fit snugly into the slots of the brackets. As the arch wire cannot rotate in the slots of the brackets, and the brackets are fixed to the incisors, a rearward force on the arch wire cannot cause tipping of the incisors.

The non-rotating relationship between the rectangular arch wire and the bracket is such that torque can be applied to the teeth by the arch wire through the brackets, when required.

One problem with the edgewise technique is that the rectangular arch wire tends to bind in the brackets on the posterior teeth as a result of excessive friction. In some cases, the friction between the arch wire and the posterior tooth brackets interferes with the action of the arch wire in correcting protrusions of the anterior teeth.

In accordance with this invention, an orthodontic arch wire is provided with posterior segments of circular cross-section and an anterior segment at least part of which is of uniform, non-circular cross-section. The circular posterior segments of the arch wire have a lesser tendency to bind in the posterior brackets. Therefore, there is a reduced likelihood that friction between the posterior tooth brackets and the arch wire will interfere with the application of a rearward force to the anterior teeth. At the same time, the non-circular cross-section of the anterior segment of the arch wire cooperates with the slots in the anterior brackets to insure rearward translation of the anterior teeth rather than tipping.

One object of the invention, therefore, is to provide an improved arch wire which either prevents tipping or applies torque to anterior teeth, and at the same time avoids interference with the rearwardly directed translational force resulting from friction between the arch wire and the posterior tooth brackets.

In accordance with the invention, the edgewise technique is advantageously carried out using an arch wire which has a slightly tapered generally trapezoidal cross-section in its anterior segment. The tapered anterior segment of the arch wire cooperates with correspondingly tapered edgewise slots in the anterior tooth brackets. The tapered anterior segment and tapered slot slide together easily but provide a tight fit so that torque can be applied through the wire to the brackets. The tapered anterior segment and tapered slot eliminate the need for extremely close manufacturing tolerances. The tapered trapezoidal cross-section is also applicable to an arch wire which has a uniform cross-section throughout its length.

It is therefore an object of the invention to provide an upward edgewise wire and bracket which apply torque, which fit together easily but securely, and which do not require special attention to tolerances in their manufacture.

In the light wire technique, as currently carried out, the arch wires have circular cross-sections. In the course of a typical correction of prominent incisors, the incisors are pulled rearwardly in the early stages of treatment even though this causes dishing. In the later stages, torque is applied to cause reverse tipping. In the light wire technique, the arch wire, rotates in the bracket because it has a circular cross-section. Therefore, in order to apply torque, it has been necessary to form special loops in the arch wire by bending or to weld, or otherwise secure, auxiliary elements to the arch wire in order to provide a two-point contact on each tooth to which torque is to be applied.

In the light wire technique, a special form of bracket is used. Whereas the edgewise bracket has a slot open to the front, the light wire bracket has a slot which is open either at the top or at the bottom. The wire enters the slot vertically and is held in the slot by a lock pin.

In accordance with the invention, the earlier stages of light wire correction are carried out in the conventional manner using an arch wire with a circular cross-section. The later stages are carried out using a special torqueing arch wire having an anterior segment at least part of which has a vertically elongated rectangular cross-section. The rectangular cross-section cooperates with the anterior tooth brackets to apply torque to the incisors to correct for the dishing effect resulting from the earlier stages of treatment.

It is desirable not to have to remove and replace brackets during the course of treatment. The need for removal and replacement of brackets is avoided by providing a bracket with two different, alternatively usable, lock pins, one pin being for a circular anterior arch wire segment, and the other pin having a surface for tightly engaging the rectangular segment of the special torqueing arch wire.

It is also an object of the invention, therefore, to provide an improved arch wire for use in the later stages of light wire treatment, which is capable of applying torque without the need for forming special loops in, or adding auxiliary elements to, the arch wire.

Various other objects will be apparent from the following detailed description when read in conjunction with the drawings.

BRIEF DESCRIPTION OF THE DRAWINGS

FIG. 1 is a top plan view of a maxillary arch wire in accordance with the invention;

FIG. 2 is a fragmentary elevational view of the arch wire of FIG. 1 showing a loop formed in the arch wire;

FIG. 3 is a vertical section taken through the arch wire of FIG. 1 on the plane 3—3;

FIG. 4 is a vertical section taken through the arch wire of FIG. 1 on the plane 4—4;

FIG. 5 is an elevational view of a posterior edgewise tooth bracket showing its relationship to a posterior segment of the arch wire of FIG. 1;

FIG. 6 is an elevational view of an anterior edgewise tooth bracket showing its relationship with an anterior segment of the arch wire of FIG. 1;

FIG. 10 is a perspective view of an arch wire in accordance with the invention for use in carrying out the later stages of light wire treatment;

FIG. 11 is a side elevation of a conventional light wire lock pin;

FIG. 12 is a side elevation of an alternative lock pin;

FIG. 13 is a side elevation, partly in section, showing an arch wire of the conventional type held in a light wire bracket;

FIG. 14 is a side elevation showing the anterior portion of an arch wire in accordance with the invention held in a light wire bracket;

DETAILED DESCRIPTION

Figure 9:
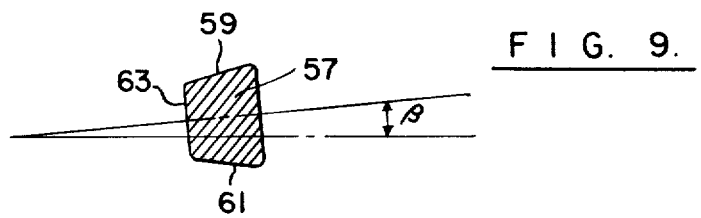
FIG. 9 is a cross-section through the tapered anterior segment of an arch wire, showing its torqueing angle.

Arch wire 10, as shown in FIG. 1 is for use in the edgewise technique. It comprises posterior segments 12 and 14, and an anterior segment 16. The anterior segment extends the width of the anterior teeth, i.e., the central and lateral incisors. The transition points between the anterior and posterior segments are indicated at 18 and 20. Immediately behind these transitions, substantially at the proximal ends of the posterior segments, loops are formed at 22 and 24. These loops are for the purpose of attaching elastic to the arch wire. They may be formed in manufacture, or can be formed by the orthodontist himself. Loop 24 is shown, in side view, in FIG. 2.

The cross-section of the posterior segments of the arch wire is circular as shown in FIG. 3, while the anterior segment is rectangular as shown in FIG. 4. The rectangular anterior segment 16 may be torqued at an angle α. Typically, the angle ranges from 0° to 15°.

The transition between the circular cross-sections and the rectangular cross-sections takes place immediately in front of the loops and approximately at the location of the transition points 18 and 20.

As shown in FIG. 5, posterior segment 14 of the arch wire is located in the rectangular slot of a posterior tooth bracket 26. This bracket is of conventional construction, having a base 28 for bonding to the tooth, and wings 30 and 32 for holding a ligature.

It is possible for segment 14 of the arch wire to rotate within the slot of bracket 26. This possibility of rotation prevents binding from occurring, and allows the wire to slide smoothly in the slot of bracket 26 as rearward force is applied to the arch wire.

In FIG. 6, anterior segment 16 of the arch wire is shown in a slot in another conventional tooth bracket 34 similar in construction to bracket 26. The height of anterior segment 16 of the arch wire is substantially equal to the height of the slot in bracket 34. This prevents relative rotation between the bracket and the arch wire. Since there can be no relative rotation, a rearward force applied by the arch wire to bracket 34 will cause the entire tooth to translate rearwardly instead of tipping inwardly.

Figure 7:
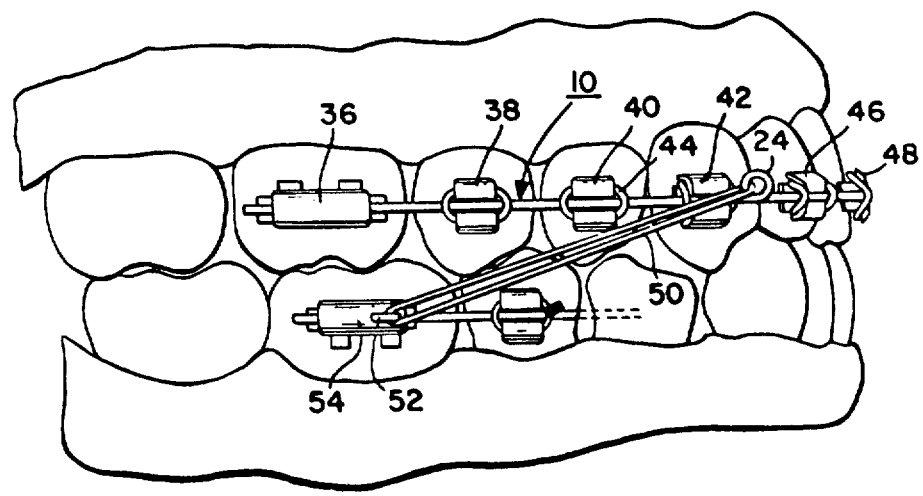
FIG. 7 is a fragmentary side elevation showing teeth of a typical patient with an arch wire in accordance with the invention fitted in edgewise brackets on the maxillary teeth.

As shown in FIG. 7, the distal portion of posterior segment 14 of arch wire 10 extends through a buccal tube 36 on the upper first molar. From there the arch wire extends through a series of brackets 38, 40, 42, 46 and 48 respectively on the second and first bicuspids, the canine, and the lateral and central incisors on the right side of the mouth. The configuration on the left side of the mouth is similar.

The transition between the circular cross-section of the posterior segment 14 of the arch wire and the rectangular configuration of anterior segment 16 is located approximately at transition point 20 between the canine and the lateral incisor. Loop 24 is formed in the circular portion of the wire at a location immediately behind transition point 20, but in front of canine bracket 42.

The transition can be at locations other than between the canine and the lateral incisor. For example the transition can be between the lateral and central incisor. The transition and the loop can be spaced from each other if desired.

An additional advantage of the invention over arch wires which are rectangular throughout is the fact that loops can be much more readily and satisfactorily formed in the circular portions of the arch wire of the invention than in conventional rectangular arch wires.

Loop 24 is connected through an elastic 50 to a cleat 52 on buccal tube 54 on a lower molar. Elastic 50 applies rearward force to arch wire 10, which in turn applies a rearwardly directed force to the anterior teeth. Since the anterior section 16 of the arch wire cannot rotate with respect to brackets 46 and 48, tipping of the incisors is prevented, and proper rearward translation takes place.

While only part of the mandibular arch wire is shown in FIG. 7, it can also be configured in accordance with the invention with circular posterior segments and a rectangular anterior segment.

The arch wire in accordance with the invention can be used with any of a large variety of standard brackets as well as with specially designed brackets.

These arch wires can be provided with appropriate offset bends where necessary, and the anterior segment can be untorqued or torqued to any desired degree. Other forms of loops or other devices for applying rearward forces to the arch wires can be provided. For example, arch wires with closing loops located behind the canines are used to close gaps, especially in cases involving extractions. The closing loops exert a rearward force on the anterior teeth, and simultaneously exert a forward force on particular posterior teeth to which distal portions of the arch wire are fixed. In this case, elastic may not be needed since rearward force on the anterior teeth is supplied by the closing loops themselves.

Figure 8:
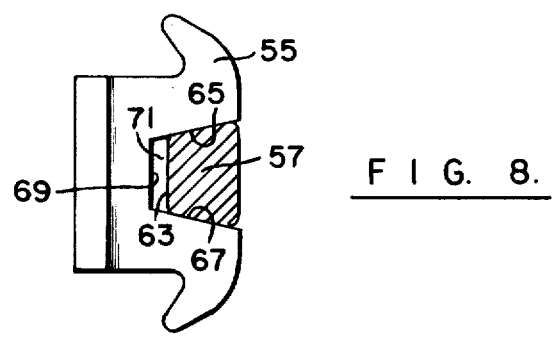
FIG. 8 is a side elevation of an anterior tooth bracket, showing its relationship to a tapered anterior segment of an arch wire.

The rectangular anterior arch wire segment shown in FIGS. 4 and 6 has the advantage that it is usable with conventional edgewise brackets. FIGS. 8 and 9 show an advantageous alternative to the rectangular cross-sectional shape of the anterior arch wire segment in which the anterior segment of the arch wire is tapered. This requires a special edgewise bracket with a tapered slot, but it affords the advantage that the arch wire segment can be fitted to the brackets more easily while achieving a secure fit.

The anterior portion 57 of the arch wire has a trapezoidal cross-sectional shape with flat upper and lower surfaces 59 and 61 converging rearwardly toward the teeth of the patient. The rear edges of flat surfaces 59 and 61 are connected by a vertical surface 63.

Segment 57 is installed in a tapered edgewise slot of a bracket 55. The slot has a flat upper surface 65, and a flat lower surface 67 facing surface 65. These surfaces converge toward the teeth of the patient and conform to surfaces 59 and 61 of the arch wire. The edges of surfaces 65 and 67 nearest the teeth are connected by a vertical surface 69. Surfaces 63 and 69 are spaced from each other when the arch wire is fully installed in the slot to provide a small gap 71 which allows the arch wire to fit tightly in the slot. The horizontal dimension of gap 71 as shown in FIG. 8 can be very small, e.g. of the order of one-thousandth of an inch.

As shown in FIG. 9, the anterior segment of the arch wire can be torqued at any desired torque angle β so that when it is installed as shown in FIG. 8 it exerts a counterclockwise torque on the bracket. As the arch wire is pulled rearwardly by elastic or other means, the flat tapered surfaces come together into conforming relationship so that the arch wire can exert a torque on the bracket in the same manner as does the arch wire of FIG. 4. Surfaces 59, 61, 65 and 67 should be flat throughout substantial portions of their areas so that the arch wire and bracket are able to fit together in only one way. The angle between upper and lower surfaces 59 and 61 of the arch wire segment should be less than approximately 30 degrees. Angles substantially greater than 30 degrees unnecessarily reduce the available contact area between the arch wire segment and the bracket.

While the trapezoidal cross-sectional shape is particularly suited to arch wires having circular posterior segments connected by a non-circular anterior segment, it is also applicable to an arch wire which has a uniform cross-section throughout its length. In the case of an arch wire which is uniform throughout, special brackets corresponding to the bracket shown in FIG. 8 are used on the posterior teeth as well as on the anterior teeth of the patient.

Whether the arch wire is trapezoidal throughout, or trapezoidal only throughout all or part of its anterior segment, the arch wire in accordance with FIGS. 8 and 9 is advantageous in that enters the bracket slot more easily than a rectangular arch wire, and yet exerts torque just as effectively as the rectangular wire. The trapezoidal wire is also advantageous because in the process of installation in the bracket, it adjusts its position automatically. The trapezoidal wire is also advantageous in that it does not require the extremely close manufacturing tolerances needed for rectangular arch wires and brackets.

Arch wire 56, as shown in FIG. 10, is for use in the later stages of treatment using the light wire technique, the earlier stages of treatment having been carried out using an arch wire having a uniform circular cross-section. Arch wire 56 comprises circular posterior sections 58 and 60, the proximal ends of which, at transition points 64 and 66 respectively, are connected by a rectangular anterior segment 62. In the cross-section of anterior segment 62, the vertical dimension is greater than the horizontal dimension, preferably by a ratio of two to one or greater. In a typical arch wire of the type shown in FIG. 10, the diameter of the cross-sections of the posterior segments is 0.018 inch, the width of the cross-sections of the anterior segment is 0.010 inch, and the height of the cross-sections of the anterior segment is 0.022 inch.

The arch wire of FIG. 10 can be used in many ways. In a typical application, it is used in the latter stages of the treatment of prominent incisors primarily to correct the "dished" effect produced by the earlier treatment stages using a conventional light wire arch having circular cross-sections throughout. When the arch wire of FIG. 10 is used for this type of treatment, anterior segment 62 is bent to exert a correcting torque on the incisors.

FIG. 11 shows a conventional lock pin 68 used in the light wire technique. This pin comprises a tapered tail 70 having a head 72 with an overhanging wire-engaging surface 74. Surface 74 can be knife-edged if desired, though this is not necessarily the case.

In FIG. 13, pin 68 is shown installed in a bracket 76 to hold a conventional circular arch wire 78 in place in slot 79, which is open at the top. The bracket is similar to a conventional light wire bracket in that it comprises a channel having a U-shaped horizontal cross-section with feet for securing the channel to a tooth. The vertical slot 79 in the channel may be somewhat deeper than the corresponding slot in a conventional light wire bracket. The tail of lock pin 70 is bent upwardly to secure the pin in the bracket. The width of slot 79 is equal to the diameter of wire 78, and head 72 of the lock pin holds the wire down against the bottom of slot 79. The wire cannot translate radially in the bracket. However, it can rotate. Thus, torque cannot be applied by the round wire.

When torque is to be applied, the round wire is removed, and replaced by an arch wire of the type shown in FIG. 10. It is desirable to form the anterior segment of the arch wire of FIG. 10 by flattening part of a round wire. This means that the width of the anterior segment 62 of the arch wire will be less than the width of bracket slot 79. Since the brackets already on the teeth by reason of earlier stages of treatment are of a size to accommodate a wire of uniform width, the new arch wire will not fit all of the brackets properly. It is, of course, desirable not to replace brackets during treatment as they are ordinarily secured to the teeth by an adhesive. The need to replace brackets is avoided by the use of an alternative lock pin 80, shown in FIG. 12. Lock pin 80 is similar to lock pin 68 in that it comprises a tapered tail 82, a head 84, and a downwardly facing wire-engaging surface 86. Underneath the head, however, there is provided an offset 88 having a wire-engaging surface 90. The lock pin is installed in bracket 76 as shown in FIG. 14. It holds anterior segment 62 of the arch wire firmly, the upper and lower surfaces being engaged by the overhanging head and the bottom of the slot respectively, and the front and rear surfaces being engaged respectively by the feet of the bracket and by surface 90 of offset 88. Offset 88 insures that the arch wire cannot rotate in the bracket. Therefore, the arch wire can apply torque to the teeth through the bracket.

Figure 15:
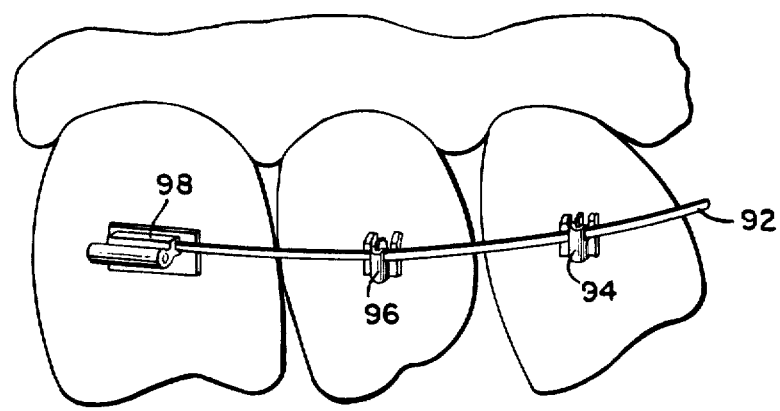
FIG. 15 is a perspective view showing teeth of a typical patient with a rectangular arch wire held in two light wire brackets and a buccal tube.
Figure 16:
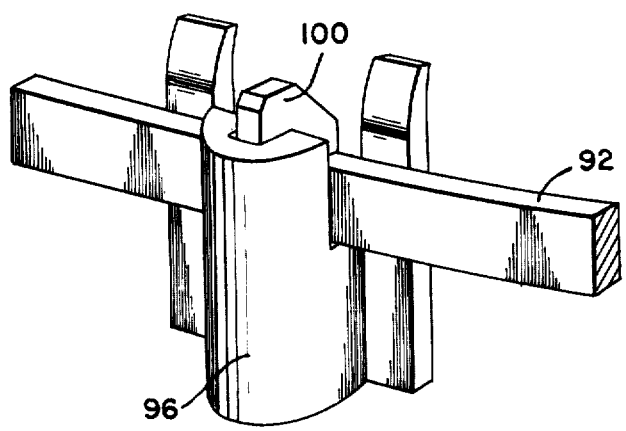
FIG. 16 is an oblique perspective view showing the details of one of the light wire brackets of FIG. 15.

Using the lock pin of FIG. 12, torque can be applied to the posterior teeth of a patient through light wire brackets, using a wire which is rectangular throughout, but not appreciably more massive than a round wire accommodated by the same brackets. The wire can have a cross-section similar to that of segment 62 of FIG. 10. As shown in FIG. 15, a wire which is rectangular throughout is used to apply torque to the bicuspids of a patient through light wire brackets 94 and 96. The distal end of the wire is held in buccal tube 98 on the first molar. The details of the manner in which wire 92 is held in bracket 96 by pin 100 are shown in FIG. 16. FIGS. 15 and 16 are merely examples of a wide variety of applications of the special lock pin.

The lock pin makes it possible to use a special light wire, having a rectangular anterior segment and circular posterior segments, to apply torque through the same light wire brackets which are used with a circular wire in an earlier stage of treatment. The pins also make it possible to apply torque to posterior teeth provided with light wire brackets.

I claim:

1. An orthodontic arch wire having posterior segments of circular cross-section and an anterior segment connecting said posterior segments, said anterior segment having a uniform, non-circular cross-section throughout substantially its entire length, in which the wire is formed into an arch having an anterior and a posterior portion and in which said non-circular cross-section has substantially flat upper and lower sides which converge toward the posterior portion of the arch.

2. An orthodontic arch wire according to claim 1 in which the angle between said upper and lower sides is less than approximately 30 degrees.

3. An orthodontic appliance comprising a series of slotted anterior brackets secured to anterior teeth of a patient, a series of slotted posterior brackets secured to posterior teeth of a patient, an arch wire extending through slots of all of said brackets, and means urging rearwardly at least the portion of the arch wire extending through the slots in the anterior brackets, the portions of the arch wire extending through slots in the posterior brackets having circular cross-sections, and the portion of the arch wire extending through slots in the anterior brackets having a uniform non-circular cross-section cooperating with the walls of the last-mentioned slots to prevent relative rotation of the arch wire and the last-mentioned slots.

4. An orthodontic appliance according to claim 3 in which said urging means urges the entire arch wire rearwardly.

5. An orthodontic appliance according to claim 3 in which said anterior and posterior brackets have non-circular edgewise slots.

6. An orthodontic appliance according to claim 5 in which said urging means urges the entire arch wire rearwardly.

7. An orthodontic appliance according to claim 5 in which said non-circular cross-section is rectangular.

8. An orthodontic appliance according to claim 5 in which the portion of the arch wire extending through the edgewise slots in the anterior brackets has substantially flat upper and lower sides which converge toward the posterior portion of the arch, and in which the edgewise slots in the anterior brackets have upper and lower surfaces which face each other and conform to said upper and lower sides respectively of the arch wire.

9. An orthodontic appliance according to claim 8 in which the angle between upper and lower sides is less than approximately 30 degrees.

10. An orthodontic appliance according to claim 8 in which the arch wire has a rearwardly facing surface extending from the rear edge of said upper side to the rear edge of said lower side, and in which each of said anterior brackets has a forwardly facing surface extending from the rear edge of its upper surface to the rear edge of its lower surface, and in which there is a gap in each bracket between the forwardly facing surface of the bracket and the rearwardly facing surface of the arch wire.

11. An orthodontic appliance according to claim 10 in which the cross-section of the portion of the arch wire extending through the edgewise slots in the anterior brackets is substantially trapezoidal.

12. An orthodontic appliance according to claim 3 in which the urging means urges rearwardly at least the portions of the arch wire which extend through said posterior brackets.

13. An orthodontic appliance comprising a series of brackets secured to the teeth of a patient, said brackets having edgewise slots, an arch wire extending through said edgewise slots, said arch wire having a substantially uniform, non-circular cross-sectional shape throughout at least a portion thereof extending through two of said brackets, said portion having substantially flat upper and lower sides which converge in the direction toward the teeth and a vertical surface facing toward the teeth of the patient and extending from the edge of said upper side nearest the teeth to the edge of said lower side nearest the teeth, and each of the edgewise slots through which said portion extends having upper and lower surfaces which face each other and conform to said upper and lower sides respectively and a vertical surface extending from the edge of said upper side nearest the teeth to the edge of said lower side nearest the teeth, and having gaps between said vertical surface of the arch wire and said vertical surfaces of the brackets.

14. An orthodontic appliance according to claim 13 in which the cross-section of said portion of the arch wire is substantially trapezoidal.

* * * * *